United States Patent
Hashimoto et al.

[11] 3,958,008
[45] May 18, 1976

[54] ANTHELMINTIC METHODS OF USE

[75] Inventors: Yoshinobu Hashimoto, Fujisawa; Kinpei Kato, Tokyo; Nobuo Sato, Chiba, all of Japan

[73] Assignee: Nippon Soda Company Limited, Tokyo, Japan

[22] Filed: Dec. 28, 1970

[21] Appl. No.: 102,081

[30] Foreign Application Priority Data
Aug. 20, 1970  Japan.............................. 45-72377

[52] U.S. Cl. .............................................. 424/300
[51] Int. Cl.² ......................................... A61K 31/27
[58] Field of Search ................................... 424/300

[56] References Cited
OTHER PUBLICATIONS
Noguchi et al. – Chem. Abst. Vol. 73 (1970) p. 14523s.
Oyamada et al. Chem. Abst. – Vol. 73 (1970) p. 109,534k.

*Primary Examiner*—Stanley J. Friedman
*Attorney, Agent, or Firm*—Howson and Howson

[57] ABSTRACT

The thioallophanate compound represented by the following general formula

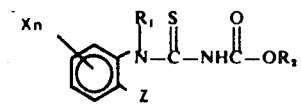

wherein X is hydrogen, chlorine atom, nitro or methyl group: Z is a substituting group selected from the group consisting of

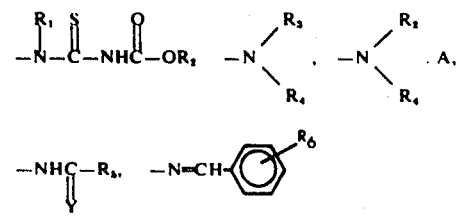

and

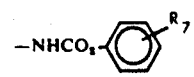

has excellent anthelmintic activity and can be used for controlling helminthiasis of animals.

3 Claims, No Drawings

ANTHELMINTIC METHODS OF USE

DETAILED EXPLANATION OF THE INVENTION

This invention relates to compositions useful against helminthiasis and more particularly concerns anthelmintic compositions containing thioallophanate as ingredient.

Helminthiasis, the infestation of the body of domestic animals such as sheep, cattle, horses, goats, pigs, poultry, dogs and cats, by various species of parasitic worms, is perhaps the most common, most serious and most widespread disease in the world. Although the economic significance of this disease has led to extensive research for new and more effective anthelmintics, most of countermeasures developed to date have not been entirely satisfactory for one or more reasons; e.g. poor therapeutic index, specificity of action, high cost, low activity, limited anthelmintic spectrum.

According to this invention, it has been found that the specific thioallophanate compounds herein described possess a significant anthelmintic activity and can be effectively employed in the treatment and/or prevention of helminthiasis.

It is one object of the present invention to provide compositions containing such substances as an active anthelmintic ingredient. It is an additional object to provide methods of using them for the purpose of controlling helminthiasis. Further objects of the invention will become apparent from the following discussion of the invention.

According to the present invention, it has been surprisingly discovered that the thioallophanate compound represented by the following general formula (1) has excellent anthelmintic activity:

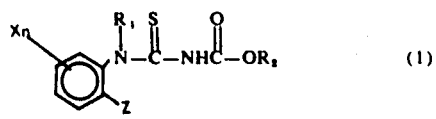

(1)

wherein X is hydrogen, chlorine atom, nitro or methyl group: Z is a substituting group selected from the group consisting of

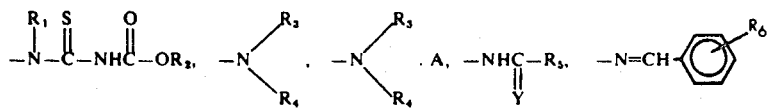

and

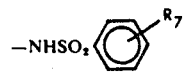

$R_1$ represents hydrogen atom or methyl group: $R_2$ represents alkyl having not more than 12 carbon atoms, alkyl having not more than 3 carbon atoms substituted with halogen, methoxy or phenyl group, alkenyl having 3 carbon atoms which may be substituted with halogen atom, methoxy or phenyl group, alkynyl having 3 carbon atoms and aryl having not more than 10 carbon atoms which may be substituted with halogen atom, nitro or methyl group: $R_3$ and $R_4$ represent hydrogen atom or lower alkyl group respectively: $R_5$ represents hydrogen atom, alkyl or cycloalkyl having not more than 4 carbon atoms, phenyl, alkoxy having not more than 4 carbon atoms, amino, alkylamino, 3,3-dimethyl-2-thioureido or 3,3-dimethylureido group: $R_6$ and $R_7$ represent hydrogen and chlorine atoms, methoxy, methyl or nitro group respectively: A represents inorganic acid or organic acid which is capable of forming a salt with an amino group: Y represents oxygen or sulfur atom: and $n$ represents an integer of $0 - 3$.

These compound can be prepared according to conventional processes. For example, the production process for the compound in which Z is

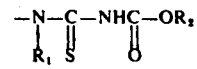

group was disclosed in the Patentblatt of German Pat. No. 1806123.9 issued on June 4, 1969 and the production process of other compounds were disclosed in the Patentblatt of German Pat. No. 1,930,540.9 issued on Jan. 8, 1970.

Typical examples of the thioallophanates which can be used in the present invention are listed in the Table 1.

| No. of Compound | Structural Formula | Chemical Name | Melting Point or Decomposition Point (d) (°C) |
|---|---|---|---|
| 1 | | 2-(3-Methoxycarbonyl-2-thioureido)-aniline | 184–185(d) |
| 2 | | 2-(3-Ethoxycarbonyl-2-thioureido)-aniline | 162–162.5(d) |
| 3 | | 2-(3-iso-Propoxycarbonyl-2-thioureido) aniline | 137–138 |

-continued

| No. of Compound | Structural Formula | Chemical Name | Melting Point or Decomposition Point (d) (°C) |
|---|---|---|---|
| 4 | (structure) | 1-(2-Amino-4-methyl-phenyl)-3-methoxy-carbonyl-2-thiourea | 167.5–168.5(d) |
| 5 | (structure) | 1-(2-Amino-5-chlorophenyl)-3-methoxycarbonyl-2-thiourea | 182–182.5(d) |
| 6 | (structure) | 1-(2-Amino-5-nitrophenyl)-3-methoxycarbonyl-2-thiourea | 202–203(d) |
| 7 | (structure) | 2-(3-Methoxycarbonyl-2-thioureido)-aniline nitrate | 153(d) |
| 8 | (structure) | 2-(3-Methoxycarbonyl-2-thioureido)-aniline oxalate | 151.5–152(d) |
| 9 | (structure) | 2-(3-Ethoxycarboyl-2-thioureido)-aniline hydrochloride | 188(d) |
| 10 | (structure) | 2-(3-Ethoxycarbonyl-2-thioureido)-aniline nitrate | 140.2–140.3(d) |
| 11 | (structure) | 2-(3-Ethoxycarbonyl-2-thioureido)-aniline oxalate | 140(d) |
| 12 | (structure) | 2-(3-Ethoxycarbonyl-2-thioureido)-aniline para-toluenesulfonate | 174(d) |
| 13 | (structure) | 2-(3-Ethoxycarbonyl-2-thioureido)-N-methyl-aniline | 171 |
| 14 | (structure) | 2-(3-Ethoxycarbonyl-2-thioureido)-N,N-dimethylaniline | 111–113 |
| 15 | (structure) | 2-(3-Ethoxycarbonyl-2-thioureido)-N,N-dimethylaniline hydrochloride | 167–168)d) |
| 16 | (structure) | 1-(3-Ethoxycarbonyl-2-thioureido)2-N,N-dimethyl-aminobenzene oxalate | 170–171 |
| 17 | (structure) | 1-Formamido-2-(3-methoxycarbonyl-2-thioureido)-benzene | 185(d) |
| 18 | (structure) | 1-Acetamido-2-(3-methoxycarbonyl-2-thioureido)-benzene | 192.5–193.5 |

-continued

| No. of Compound | Structural Formula | Chemical Name | Melting Point or Decomposition Point (d) (°C) |
|---|---|---|---|
| 19 | [phenyl-NH-C(=S)-NH-C(=O)-O-C₂H₅; NH-C(=O)-C₂H₅] | 1-Propionamido-2-(3-ethoxycarbonyl-2-thioureido)-benzene | 170–171.5 |
| 20 | [phenyl-NH-C(=S)-NH-C(=O)-O-CH₃; NH-C(=O)-cyclopropyl] | 1-Cyclopropancarbonamido-2-(3-methoxycarbonyl-2-thioureido)-benzene | 191–192(d) |
| 21 | [phenyl-NH-C(=S)-NH-C(=O)-O-C₂H₅; NH-C(=O)-cyclohexyl] | 1-Benzamido-2-(3-ethoxycarbonyl-2-thioureido)-benzene | 192–193 |
| 22 | [phenyl-NH-C(=S)-NH-C(=O)-O-C₂H₅; NH-C(=O)-O-CH₃] | 1-Methoxycarbonamido-2-(3-ethoxycarbonyl-2-thioureido)-benzene | 168–170(d) |
| 23 | [phenyl-NH-C(=S)-NH-C(=O)-O-CH₃; NH-C(=O)-O-C₂H₅] | 1-Ethoxycarbonamido-2-(3-methoxycarbonyl-2-thioureido)-benzene | 147–149(d) |
| 24 | [phenyl-NH-C(=S)-NH-C(=O)-O-CH₃; NH-C(=O)-NH-C₃H₇] | 1-(3-n-Propylureido)-2-(3-methoxycarbonyl-2-thioureido)-benzene | 132.5–133.5 |
| 25 | [phenyl-NH-C(=S)-NH-C(=O)-O-CH₃; NH-C(=O)-NH-C₄H₉] | 1-(3-n-Butylureido)-2-(3-methoxycarbonyl-2-thioureido)-benzene | 182–183 |
| 26 | [phenyl-NH-C(=S)-NH-C(=O)-O-C₂H₅; NH-C(=O)-NH-C₄H₉] | 1-(3-n-Butylureido)-2-(3-ethoxycarbonyl-2-thioureido)-benzene | 182 |
| 27 | [phenyl-NH-C(=S)-NH-C(=O)-O-C₂H₅; NH-C(=O)-H] | 1-Thioformamido-2-(3-ethoxycarbonyl-2-thioureido)-benzene | 172 |
| 28 | [phenyl-NH-C(=S)-NH-C(=O)-O-C₂H₅; NH-C(=S)-NH₂] | 1-(2-Thiocarbamoyl-aminophenyl)-3-ethoxycarbonylthiourea | 157(d) |
| 29 | [phenyl-NH-C(=S)-NH-C(=O)-O-C₂H₅; NH-C(=S)-NH-CH₃] | 1-(3-Ethoxycarbonyl-2-thioureido)-2-(3-methyl-2-thioureido)-benzene | 160–161 |
| 30 | [phenyl-NH-C(=S)-NH-C(=O)-O-C₂H₅; NH-C(=S)-NH-C₃H₇] | 1-(3-n-Propyl-2-thioureido)-2-(3-ethoxycarbonyl-2-thioureido)-benzene | 132.5–133.5(d) |
| 31 | [phenyl-NHC(=S)NHCOOCH₃; NHC(=S)NH-C(=S)-N(CH₃)₂] | 1-(3-N,N-Dimethylamino-2-thiocarbonyl-2-thioureido)-2-(3-methoxycarbonyl-2-thioureido)-benzene | 149(d) |

-continued

| No. of Compound | Structural Formula | Chemical Name | Melting Point or Decomposition Point (d) (°C) |
|---|---|---|---|
| 32 | (structure) | 1-(3-N,N-Dimethylaminothio-carbonyl-2-thioureido)-2-(3-ethoxycarbonyl-2-thioureido)-benzene | 148–149(d) |
| 33 | (structure) | 1-(3-N,N-Dimethylamino-carbonyl-2-thioureido)-2-(3-methoxycarbonyl-2-thioureido)-benzene | 159–160(d) |
| 34 | (structure) | 1-Benzylidenamino-2-(3-methoxycarbonyl-2-thioureido)-benzene | 145–146 |
| 35 | (structure) | 1-(4-Chlorobenzylidenamino)-2-(3-methoxycarbonyl-2-thioureido)-benzene | 183–183.5(d) |
| 36 | (structure) | 1-(4-Methoxybenzyliden-amino)-2-(3-methoxycarbonyl-2-thioureido)-benzene | 159–159.5(d) |
| 37 | (structure) | 1-(3-Nitrobenzyliden-amino-2-(3-ethoxycarbonyl-2-thioureido)-benzene | 185(d) |
| 38 | (structure) | 1-Benzenesulfonicamido-2-(3-methoxycarbonyl-2-thioureido)-benzene | 197–198(d) |
| 39 | (structure) | 1-(4-Toluenesulfonicamido)-2-(3-ethoxycarbonyl-2-thioureido)-benzene | 179–180(d) |
| 40 | (structure) | 1-(4-Chlorobenzenesulfonic-amodo)-2-(3-methoxycarbonyl-2-thioureido)-benzene | 192–193(d) |
| 41 | (structure) | 2(3-Allyloxycarbonyl-2-thioureido)-aniline | 138–139 |

-continued

| No. of Compound | Chemical Name | Melting Point or Decomposition Point (d) (°C) |
|---|---|---|
| 42 | 1,2-Bis(3-methoxycarbonyl-2-thioureido)-benzene | 181.5–182.5(d) |
| 43 | 1,2-Bis(3-ethoxycarbonyl-2-thioureido)-benzene | 195(d) |
| 44 | 1,2-Bis(3-isopropoxy-carbonyl-2-thioureido)-benzene | 205–206(d) |
| 45 | 1,2-Bis(3-isobutoxycarbonyl-2-thioureido)-benzene | 197–198(d) |
| 46 | 3,4-Bis(3-ethoxycarbonyl-2-thioureido) toluene | 175–176(d) |
| 47 | 1,2-Bis(3-ethoxycarbonyl-2-thioureido)-4-chlorobenzene | 170.5–171.5(d) |
| 48 | 1,2-Bis(3-ethoxycarbonyl-2-thioureido)-4-nitrobenzene | 205–205.5(d) |
| 49 | 1,2-Bis(3-ethoxycarbonyl-2-thioureido)-4,5-dichlorobenzene | 206–207(d) |
| 50 | 1,2-Bis(3-ethoxycarbonyl-2-thioureido)-3,4,6-trichlorobenzen | 180–181 |
| 51 | 1,2-Bis(3-benzyloxy-carbonyl-2-thioureido)-benzene | 171–172 |
| 52 | 1,2-Bis[3-(-β-Methoxy)ethoxycarbonyl-2-thioureido] benzene | 170.5–171.5 |
| 53 | 1,2-Bis[3-(β-chloroethoxycarbonyl)-2-thioureido] benzene | 181–182(d) |

-continued

| No. of Compound | Structural Formula | Chemical Name | Melting Point or Decomposition Point (d) (°C) |
|---|---|---|---|
| 54 | | 1,2-Bis[(3-ethylthio)-carbonyl-2-thioureido] benzene | 191–192(d) |
| 55 | | 1,2-Bis[3-dodecylthio) carbonyl]-thioureido-benzene | 122–123.5(d) |
| 56 | | 1,2-Bis(3-allyloxycarbonyl-2-thioureido) benzene | 166–167 |
| 57 | | 1,2-Bis[3-(2-Propynyloxy-carbonyl)-2-thioureido] benzene | 172–173(d) |
| 58 | | 1,2-Bis[3-(4-chlorophenoxy-carbonyl)-2-thioureido] benzene | 193(d) |
| 59 | | 1,2-Bis[3-(4-nitrophenoxy-carbonyl)-2-thioureido] benzene | 186(d) |
| 60 | | 1,2-Bis[3-(4-methylphenoxy-carbonyl)-2-thioureido]-4-chlorobenzene | 191–192(d) |
| 61 | | 3,4-Bis[3-(4-chlorophenoxy-carbonyl)-2-thioureido]-toluene | 199–200(d) |
| 62 | | 1,2-Bis[3-(2-naphthoxy-carbonyl)-2-thioureido] benzene | 191–192(d) |
| 63 | | 1,2-Bis[3-(2-naphthoxy-carbonyl)-2-thioureido]-4'-nitrobenzene | 180(d) |
| 64 | | 1-(3-Ethoxycarbonyl-2-throureido)-2-(3-ethoxycarbonyl-1-methyl-2-throureido)-benzene | 176–177(d) |

-continued

| No. of Compound | Structural Formula | Chemical Name | Melting Point or Decomposition Point (d) (°C) |
|---|---|---|---|
| 65 | (structure) | 1,2-Bis(3-ethoxycarbonyl-1-methyl-2-thioureido)benzene | |
| 66 | (structure) | 1-(3-Ethoxycarbonyl-2-thioureido)-2-(3-methoxy-carbonyl-2-thioureido)-benzene | 177–178(d) | note: Symbol (d) means decomposition

The above compound may be used in connection with any carrier vehicle and in the form of a solution, capsule, tablet or bolus.

Among the compounds employed as an ingredient of this invention, the salts (e.g. compound 7 ~ 12, 15, 16) have high solubility in water and then they can be added to the drinking water just before use, or a drench formulation can be prepared in advance which may be diluted up to the desired concentration. When the composition of the present invention is in the form of solution, liquid media, e.g. alcohols, acetone, dimethyl sulfoxide, dimethylformamide, dioxane and cyclohexanone can be used. In the drench or solution preparation, concentrations may be 10% – 40% wt/vol. The exact percentage used will depend upon the dosage level required and the limitation imposed on the volume to be administered.

When administered in powdered form, the anthelmintic ingredient may be dispersed in or admixed with standard elements of animal sustenance, such as feed, or other orally ingestible carriers, such as distiller's dried grains, corn meal, alfalfa, ground oyster shells, molasses solubles, or corn cob meal. This method is generally used when it is desired to administer the compounds either as therapeutic or prophylactic use over an extended period.

When the composition is used in the solid dosage forms such as a capsule, tablet, or bolus, the ingredient may be conveniently mixed with any other acceptable vehicles including diluents, fillers, binders and lubricants in the preparation of such forms, and preferably materials nutritionally suitable such as starch, lactose, magnesium stearate, vegetable gums, hydroxy alkyl cellulose and the like.

The proportion of the anthelmintic ingredients in the above forms of administration may vary widely depending upon the desired dosage sought to be administered to the infected host. Thus, tablets and boluses, whether enteric in nature or not, can incorporate, for example, in the ranges from 5%, to 80% of the anthelmintic ingredient by weight of the total composition. Although the dosage rate varies depending on the mode of treatment, the activity of the components, the size of the host and the severity of infection, when single unit dosage forms such as tablets, boluses, or drenches are desired to be administered to the animal, suitable results are obtained when the compositions contain enough of the anthelmintic ingredients of the present invention to provide a dosage level of from 0.1 ~ 1000 and preferably 5 ~ 500mg/Kg of animal body weight.

If desired, the course of treatment may be extended over a period of days in which case the optimum daily dose level is reduced.

The following examples are given for the purpose of illustration only.

EXAMPLE 1

A bolus having the following composition suitable for oral administration was prepared.

| | | |
|---|---|---|
| Compound (1) | 10 | parts by weight |
| Dicalcium phosphate | 3 | '' |
| Starch | 1.5 | '' |
| Gum | 0.3 | '' |
| Talc | 1 | '' |
| Mg stearate | 0.1 | '' |

The dicalcium phosphate was thoroughly mixed with the compound 1 and the mixture was pulverized to a particle size of less than 90 mesh. 1 part of starch was added to the mixture in the form of an aqueous starch paste and the resulting mixture was granulated in the usual manner. The granules were dried at 50°C. The guar gum and the balance of the starch were added and the mixture thoroughly blended. The remainder of the ingredients were then added and the whole completely mixed and compressed.

EXAMPLE 2.

A drench having the following composition

| | | |
|---|---|---|
| Compound 2 | 10 | parts by weight |
| Polyoxyethylene alkylphenol ether | 0.1 | '' |
| Silicone oil | 0.02 | '' |
| Starch | 15.0 | '' | was prepared by blending the ingredients into dry mix and the resulting mixture was added to 300ml. of water gradually.

EXAMPLE 3.

A drench having the following composition was prepared by usual formulating methods.

| | | |
|---|---|---|
| Compound 4 | 10 | parts by weight |

| | | |
|---|---|---|
| Silicone oil | 0.02 | " |
| Hydroxy propyl cellulose | 1.2 | " |
| Water | 150 | " |

EXAMPLE 4.

Tablets having the following composition were prepared by the conventional process.

| | | |
|---|---|---|
| Compound 25 | 10 | parts by weight |
| Calcium phosphate | 8 | " |
| Hydroxypropyl cellulose | 1.5 | " |
| Lactose | 80 | " |

Hydroxypropylcellulose was dissolved into alcohol and the resulting solution was sprayed to the dry mix of the ingredients. After removing the solvent, the mixture was granulated in the usual manner and compressed to tablets having 0.2g of weight.

EXAMPLE 5.

Feed supplements according to the following compositions were prepared by the conventional process.

| | | |
|---|---|---|
| (1) | Compound 12 | 15 |
| | Exoleated soybean | 85 |
| (2) | Compound 42 | 5 |
| | Wheat bran | 95 |
| (3) | Compound 43 | 10 |
| | Rice bran | 90 |
| (4) | Compound 44 | 25 |
| | Corn grain | 75 |

EXAMPLE 6.

50 parts of compound 66 was mixed with 50 parts of tricalcium phosphate. Then the resulting powder was subdivided and loaded into hard gelatin capsules in such a manner that each capsule contains the equivalent of 200mg of the active ingredient.

EXAMPLE 7.

The anthelmintic ingredients listed in Table 2 were mixed with the dog food consisting of imitation meat. The dogs naturally infected with toxocara canis were divided into groups consisting of three dogs and after checking the number of eggs in 1g of excrement of each dog, the above food was fed in such manner that the each dog received 50mg of the anthelmintic ingredient/Kg of body weight/day for 3 days. Egg counts were made on the third day following the last treatment. Results are tabulated below in Table 2.

Table 2

| Compound | Dosage | Eggs (average) | |
|---|---|---|---|
| | | Before Medication | After Medication |
| 1 | 50mg/Kg/day | 3,960 | 0 |
| 2 | " | 4,110 | 0 |
| 4 | " | 4,120 | 160 |
| 8 | " | 3,780 | 0 |
| 9 | " | 3,900 | 0 |
| 13 | " | 4,100 | 175 |
| 16 | " | 3,970 | 205 |
| 17 | " | 4,250 | 0 |
| 18 | " | 4,080 | 35 |
| 20 | " | 3,890 | 5 |

Table 2-continued

| Compound | Dosage | Eggs (average) | |
|---|---|---|---|
| | | Before Medication | After Medication |
| 21 | " | 4,040 | 125 |
| 22 | " | 3,770 | 10 |
| 25 | " | 3,810 | 50 |
| 27 | " | 4,200 | 35 |
| 29 | " | 4,190 | 145 |
| 30 | " | 3,920 | 210 |
| 31 | " | 3,750 | 190 |
| 33 | " | 4,150 | 205 |
| 34 | " | 4,130 | 180 |
| 35 | " | 3,920 | 75 |
| 36 | " | 4,030 | 65 |
| 38 | " | 4,050 | 5 |
| 39 | " | 3,860 | 0 |
| 41 | " | 4,260 | 55 |
| 42 | " | 5,200 | 175 |
| 43 | " | 4,850 | 0 |
| 56 | " | 5,150 | 185 |
| 66 | " | 4,920 | 155 |
| Piperazine | 200mg/Kg/day | 4,780 | 535 |
| Control | None | 4,860 | 4,800 |

No secondary effect or change on excrement, blood and appetite was observed.

EXAMPLE 8.

Oral administration of the anthelmintic ingredients as a drench according to the composition of Example 2 to sheep which were naturally infected with gastrointestinal nematodes was performed for three days at levels of 50mg of the anthelmintic ingredient /Kg of body weight/day. A dose of the same ingredients was given to a group consisting of three sheep and the results of the egg count before and after third day of treatment are tabulated below in Table 3.

Table 3

| Compound | Dosage | Eggs (average) | |
|---|---|---|---|
| | | Before Medication | After Medication |
| 1 | 50mg/Kg/day | 2,410 | 0 |
| 2 | " | 2,940 | 0 |
| 3 | " | 2,500 | 120 |
| 5 | " | 2,050 | 80 |
| 6 | " | 2,420 | 105 |
| 7 | " | 2,770 | 40 |
| 8 | " | 2,490 | 0 |
| 9 | " | 2,130 | 0 |
| 10 | " | 2,640 | 0 |
| 11 | " | 2,280 | 0 |
| 12 | " | 1,960 | 125 |
| 13 | " | 2,500 | 140 |
| 14 | " | 3,450 | 75 |
| 15 | " | 2,750 | 160 |
| 17 | " | 2,120 | 0 |
| 18 | " | 2,850 | 80 |
| 19 | " | 1,970 | 105 |
| 22 | " | 2,300 | 55 |
| 23 | " | 2,570 | 115 |
| 24 | " | 1,980 | 180 |
| 25 | " | 3,080 | 70 |
| 26 | " | 1,910 | 0 |
| 27 | " | 2,570 | 40 |
| 28 | " | 3,110 | 75 |
| 29 | " | 2,640 | 205 |
| 30 | " | 2,530 | 0 |
| 34 | " | 2,010 | 160 |
| 37 | " | 2,530 | 0 |
| 40 | " | 2,900 | 0 |
| 41 | " | 2,370 | 60 |
| 42 | " | 2,470 | 0 |
| 43 | " | 1,990 | 0 |
| 44 | " | 3,250 | 115 |
| 45 | " | 2,400 | 180 |
| 46 | " | 2,540 | 120 |
| 48 | " | 1,900 | 45 |
| 49 | " | 2,690 | 160 |
| 50 | " | 2,540 | 125 |
| 51 | " | 3,080 | 80 |
| 52 | " | 2,130 | 55 |
| 53 | " | 2,440 | 0 |

Table 3-continued

| Compound | Dosage | Eggs (average) Before Medication | Eggs (average) After Medication |
|---|---|---|---|
| 54 | " | 1,970 | 190 |
| 55 | " | 2,750 | 180 |
| 56 | " | 3,100 | 125 |
| 57 | " | 2,500 | 100 |
| 58 | " | 2,200 | 0 |
| 59 | " | 2,450 | 85 |
| 60 | " | 1,910 | 0 |
| 61 | " | 2,760 | 0 |
| 62 | " | 2,070 | 190 |
| 63 | " | 2,430 | 90 |
| 64 | " | 3,400 | 125 |
| 65 | " | 2,290 | 40 |
| 66 | " | 2,850 | 0 |
| Control | None | 2,280 | 2310 |
| " | None | 3,250 | 3010 |
| " | None | 2,890 | 2960 |

No secondary effect or change on excrement, blood and appetite was observed.

What is claimed is:

1. A method for the treatment of helminth infections in man and domestic animals which comprises administering to man or a domestic animal infected with helminths an anthelmintically effective amount of a benzene derivative selected from the group consisting of:

2-(3-ethoxycarbonyl-2-thioureido)-N,N-dimethylaniline,
2-(3-ethoxycarbonyl-2-thioureido)-N,N-dimethylaniline hydrochloride,
1-(3-ethoxycarbonyl-2-thioureido)2-N,N-dimethylamino-benzene oxalate,
1-formamido-2-(3-methoxycarbonyl-2-thioureido)-benzene,
1-acetamido-2-(3-methoxycarbonyl-2-thioureido)-benzene,
1-propionamido-2-(3-ethoxycarbonyl-2-thioureido)-benzene,
1-cyclopropancarbonamido-2-(3-methoxycarbonyl-2-thioureido)-benzene,
1-benzamido-2-(3-ethoxycarbonyl-2-thioureido)-benzene,
1-methoxycarbonamido-2-(3-ethoxycarbonyl-2-thioureido)-benzene,
1-ethoxycarbonamido-2-(3-methoxycarbonyl-2-thioureido)-benzene,
1-(3-n-propylureido)-2-(3-methoxycarbonyl-2-thioureido)-benzene,
1-(3-n-butylureido)-2-(3-methoxycarbonyl-2-thioureido)-benzene,
1-(3-n-butylureido)-2-(3-ethoxycarbonyl-2-thioureido)-benzene,
1-thioformamido-2-(3-ethoxycarbonyl-2-thioureido)-benzene,
1-(2-thiocarbamoyl-aminophenyl)-3-ethoxycarbonylthiourea,
1-(3-ethoxycarbonyl-2-thioureido)-2-(3-methyl-2-thioureido)-benzene,
1-(3-n-propyl-2-thioureido)-2-(3-ethoxycarbonyl-2-thioureido)-benzene,
1-(3-N,N-dimethylamino-2-thiocarbonyl-2-thioureido)-2-(3-methoxycarbonyl-2-thioureido)-benzene,
1-(3-N,N-dimethylaminothiocarbonyl-2-thioureido)-2-(3-ethoxycarbonyl-2-thioureido)-benzene,
1-(3-N,N-dimethylamino-carbonyl-2-thioureido)-2-(3-methoxycarbonyl-2-thioureido)-benzene,
1-benzylidenamino-2-(3-methoxycarbonyl-2-thioureido)-benzene,
1-(4-chlorobenzylidenamino)-2-(3-methoxycarbonyl-2-thioureido)-benzene,
1-(4-methoxybenzylidenamino)-2-(3-methoxycarbonyl-2-thioureido)-benzene,
1-(3-nitrobenzylidenamino-2-(3-ethoxycarbonyl-2-thioureido)-benzene,
1-benzenesulfonicamido-2-(3-methoxycarbonyl-2-thioureido)-benzene,
1-(4-toluenesulfonicamido)-2-(3-ethoxycarbonyl-2-thioureido)-benzene
1(4-chlorobenzenesulfonicamodo)-2-(3-methoxycarbonyl-2-thioureido)-benzene,
1,2-bis(3-benzyloxycarbonyl-2-thioureido)-benzene,
1,2-bis[3-($\beta$-methoxy) ethoxycarbonyl-2-thioureido]benzene,
1,2-bis]3-($\beta$-chloroethoxycarbonyl)-2-thioureido]-benzene,
1,2-bis(3-allyloxycarbonyl-2-thioureido)benzene,
1,2-bis[3-(2-propynyloxycarbonyl)-2-thioureido]benzene,
1,2-bis[3-(4-chlorophenoxycarbonyl)-2-thioureido]-benzene,
1,2-bis[3-(4-nitrophenoxycarbonyl)-2-thioureido]-benzene,
1,2-bis[3-(4-methylphenoxycarbonyl)-2-thioureido]-4-chlorobenzene,
3,4-bis[3-(4-chlorophenoxycarbonyl)-2-thioureido]-toluene,
1,2-bis[3-(2-naphthoxycarbonyl)-2-thioureido]benzene and
1,2-bis[3-(2-naphthoxycarbonyl)-2-thioureido]-4'-nitrobenzene.

2. A method for the treatment of helminth infections according to claim 1 wherein the benzene derivative is administered orally.

3. A method for the treatment of helminth infection in domestic animals according to claim 1 in which the benzene derivative is administered orally and wherein the dosage of the benzene derivative is from about 0.1 to 1000 mg. per Kg. of normal body weight.

* * * * *